(12) United States Patent
Nakatsuji et al.

(10) Patent No.: US 10,087,284 B2
(45) Date of Patent: Oct. 2, 2018

(54) FLUORINE-CONTAINING POLYMERIZABLE MONOMER AND POLYMER COMPOUND USING SAME

(71) Applicant: Central Glass Company, Limited, Ube-shi, Yamaguchi (JP)

(72) Inventors: Junya Nakatsuji, Fujimino (JP); Makoto Matsuura, Ibaraki (JP); Kazuhiro Yamanaka, Tachikawa (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/375,522

(22) Filed: Dec. 12, 2016

(65) Prior Publication Data

US 2017/0088666 A1    Mar. 30, 2017

Related U.S. Application Data

(62) Division of application No. 14/122,578, filed as application No. PCT/JP2012/063781 on May 29, 2012, now Pat. No. 9,550,711.

(30) Foreign Application Priority Data

May 30, 2011    (JP) .................................. 2011-121030
May 24, 2012    (JP) .................................. 2012-118432

(51) Int. Cl.
      *C08G 63/682*    (2006.01)
(52) U.S. Cl.
      CPC .............................. *C08G 63/6826* (2013.01)
(58) Field of Classification Search
      None
      See application file for complete search history.

(56) References Cited

U.S. PATENT DOCUMENTS

| 3,634,456 A | 1/1972 | Chen et al. |
| 5,118,874 A | 6/1992 | Appel et al. |
| 2010/0029895 A1 | 2/2010 | Narizuka et al. |
| 2011/0301305 A1 | 12/2011 | Isono et al. |
| 2013/0085237 A1 | 4/2013 | Narizuka et al. |
| 2014/0194655 A1 | 7/2014 | Nakatsuji et al. |

FOREIGN PATENT DOCUMENTS

| JP | 50-15258 | 6/1975 |
| JP | 2006-206879 A | 8/2006 |
| JP | 2007-119503 A | 5/2007 |
| JP | 2007-119504 A | 5/2007 |
| JP | 2008-150534 A | 7/2008 |
| JP | 2010-215904 A | 9/2010 |

OTHER PUBLICATIONS

Soulen, R., et al, "Preparation of 1,3,5-Tris (2-Hydroxyhexafkuoro-2-Propyl) Benzene and Some of Its Derivatives", Journal of Fluorine Chemistry, 1989. vol. 44, pp. 203-210 (Eight (8) pages).
Farah, B., "Perhalo Ketones, VII, Phenolic Derivatives of the Perhaloacetones", Journal of Organic Chemistry, Apr. 1965, vol. 30, No. 4, pp. 1003-1005 (Three (3) pages).
International Search Report (PCT/ISA/210) issued in PCT Application No. PCT/JP2012/063781 dated Sep. 11, 2012 with English translation (Seven (7) pages).
Japanese-language Written Opinion (PCT/ISA/210) issued in PCT Application No. PCT/JP2012/063781 dated Sep. 11, 2012 (Four (4) pages).

*Primary Examiner* — Megan McCulley
(74) *Attorney, Agent, or Firm* — Crowell & Moring LLP

(57) ABSTRACT

Disclosed in the present invention are a fluorine-containing polymerizable compound of the general formula (1) and a polymer compound obtained therefrom:

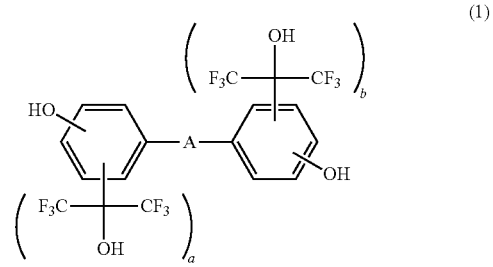

(1)

where A represents a single bond, an oxygen atom, a sulfur atom, $SO_2$, $CH_2$, CO, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorene; and a and b each independently represent an integer of 0 to 2 and satisfy a relationship of $1 \leq a+b \leq 4$.
The thus-obtained polymer compound combines adequate hydrophilicity and high transparency with low water adsorption of fluorine-containing compound.

5 Claims, No Drawings

FLUORINE-CONTAINING POLYMERIZABLE MONOMER AND POLYMER COMPOUND USING SAME

CROSS REFERENCE TO RELATED APPLICATIONS

This application is a divisional of and claims priority to U.S. application Ser. No. 14/122,578, filed Nov. 26, 2013, which is a National Stage of PCT/JP2012/0063781, filed May 29, 2012, which claims priority to Japanese Patent Application No. 2012-118432, filed May 24, 2012, which claims priority to Japanese Patent Application No. 2011-121030, filed May 30, 2011, the disclosures of which are expressly incorporated by reference herein.

TECHNICAL FIELD

The present invention relates to a fluorine-containing polymerizable monomer and a polymer compound obtained therefrom, which are useful as resist materials for lithography in semiconductor manufacturing processes, coatings for flat panel displays, protection films for substrates in electronic circuit boards, protection films for semiconductors and the like.

BACKGROUND ART

Bisphenols are useful as raw materials of engineering plastics. Polymers using bisphenols are suitable in a wide range of applications such as electronic components, separation films for water treatment, gas separation and hemodialysis etc. However, polyesters having bisphenol repeating units are difficult to dissolve in organic solvents and difficult to mold.

There have thus been developed fluorine-containing polymers using, as monomers, bisphenols or dicarboxylic acids each having a hexafluoroisopropylidene group, i.e., $C(CF_3)_2$ in the respective chemical structures for improvement in organic solvent solubility (see Non-Patent Document 1). The thus-obtained fluorine-containing polymers feature good heat resistance, corrosion resistance, water repellency, low water absorption, low dielectric constant, low refractive index and the like.

Further, a fluorocarbinol group is known as a functional group to impart adequate hydrophilicity to fluorine compounds. In particular, a resist resin using a fluorine compound with a 2-hydroxy-1,1,1,3,3,3-hexafluoroisopropyl group, i.e., $C(CF_3)_2OH$ group (hereinafter sometimes referred to as "HFIP group") as a raw material shows high transparency and good substrate adhesion when used for lithographic patterning in semiconductor manufacturing processes. When this fluorine compound is used as a resist resin for photolithography, the resist resin shows high sensitivity for exposure to short-wavelength ultraviolet irradiation with the use of an argon fluoride laser (wavelength: 193 nm) etc. as an irradiation source as well as solubility in developers for patterning after the exposure.

As HFIP-containing aromatic polymers, aromatic polyamide or polyimide compounds with HFIP groups have been disclosed (see Patent Documents 1 to 4). It is described in Patent Documents 1 to 4 that the introduction of HFIP groups to aromatic polyamide or polyimide compounds allows improvement in organic solvent solubility and reduction in dielectric constant. It is also described that: in the case of using, as a raw material of HFIP-containing aromatic polyamide or polyimide compounds, a diamine monomer in which HFIP group and amino group are respectively attached to ortho-position carbon atoms, the HFIP-containing aromatic polyamide can be converted to a specific polymer compound of fluorine-containing heterocyclic ring (heteroring) structure by heating and dehydrating the HFIP-containing aromatic polyamide; and this conversion reaction allows further reduction in water absorption and dielectric constant and improvement in heat resistance due to the disappearance of polar hydroxyl groups.

Although the HFIP-containing aromatic polyamide or polyimide compounds have been disclosed as mentioned above, polymers of these aromatic compounds are low in transparency regardless of their high fluorine contents. One reason for such low transparency is that the π conjugated systems of the respective compounds become long in length by the formation of imide rings or heterocyclic rings. Highly transparent materials are usable as not only resist materials but also coatings for flat panel displays, protection films for substrates in electronic circuit boards, protection films for semiconductors and the like.

There is a report about HFIP-containing phenol derivatives (see Non-Patent Document 2) as fluorine-containing compounds in which HFIP groups are added to aromatic polyesters. However, detailed analyses of these compounds, such as identification of the position of substitution of the HFIP groups on the aromatic rings, have not been carried out. Further, there is no report about polymers using fluorine-containing phenolic compounds as fluorine-containing polymerizable monomers. As mentioned above, HFIP-containing aromatic polyesters are expected as polymer materials that combine adequate hydrophilicity with low water adsorption and good transparency of fluorine-containing compounds.

Non-Patent Document 3 discloses the substitution of a hydrogen atom of the HFIP group.

PRIOR ART DOCUMENTS

Patent Documents

Patent Document 1: Japanese Laid-Open Patent Publication No. 2006-206879
Patent Document 2: Japanese Laid-Open Patent Publication No. 2007-119503
Patent Document 3: Japanese Laid-Open Patent Publication No. 2007-119504
Patent Document 4: Japanese Laid-Open Patent Publication No. 2008-150534

Non-Patent Documents

Non-Patent Document 1: Advanced Polymer Material Series 2, "High-Performance Aromatic Polymers", Society of Polymer Science, p. 131
Non-Patent Document 2: Journal of Organic Chemistry, vol. 30, p. 1004 (1965)
Non-Patent Document 3: Journal of Fluorine Chemistry, 44 (1989), p. 203-210

SUMMARY OF THE INVENTION

Problems to be Solved by the Invention

It is an object of the present invention to provide a fluorine-containing polymerizable monomer capable of forming a fluorine-containing polymer compound that combines hydrophilicity of hydroxy group with low absorption of fluorine-containing polymer. It is also an object of the present invention to provide a fluorine-containing polymerizable monomer capable of forming a fluorine-containing polymer compound that not only combines adequate hydrophilicity with low water adsorption of fluorine-containing compound, but also shows high transparency as compared to conventional aromatic polyamide or polyimide compounds with HFIP groups.

Means for Solving the Problems

As means for solving the above-mentioned problems, the present inventors have obtained a fluorine-containing aromatic phenolic compound with a HFIP group(s) as a novel fluorine-containing polymerizable monomer and further obtained a fluorine-containing aromatic polyester with HFIP groups as a novel polymer compound by polymerization of the fluorine-containing polymerizable monomer. The present invention is based on these extensive research results.

The fluorine-containing polyester shows high transparency when no heterocyclic ring is contained in the fluorine-containing polyester. The thus-obtained novel fluorine-containing aromatic polyester with no heterocyclic ring structure shows much higher transparency than those of conventional aromatic polyamide or polyimide compounds with HFIP groups. Herein, the term "phenolic compound" refers to a compound in which a hydrogen atom on aromatic ring is substituted with a hydroxyl group in the present invention.

Namely, the present invention includes the following aspects.

[Inventive Aspect 1]

A fluorine-containing polymerizable monomer of the general formula (1):

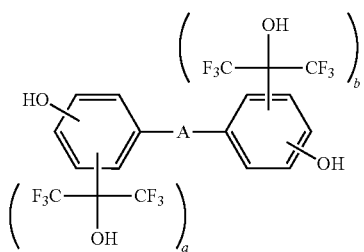
(1)

where A represents a single bond, an oxygen atom, a sulfur atom, $SO_2$, $CH_2$, CO, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorine; and a and b each independently represent an integer of 0 to 2 and satisfy a relationship of 1≤a+b≤4.

[Inventive Aspect 2]

The fluorine-containing polymerizable monomer according to Inventive Aspect 1, wherein the fluorine-containing polymerizable monomer of the general formula (1) is of the general formula (2):

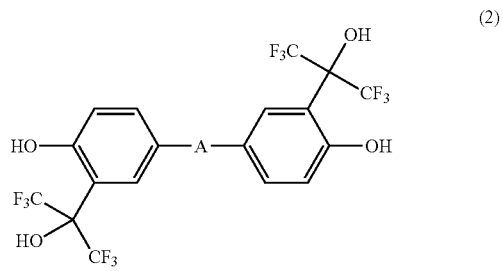
(2)

where A represents a single bond, an oxygen atom, a sulfur atom, $SO_2$, $CH_2$, CO, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorine.

[Inventive Aspect 3]

The fluorine-containing polymerizable monomer according to Inventive Aspect 2, wherein the fluorine containing polymerizable monomer of the general formula (2) is of the formula (3):

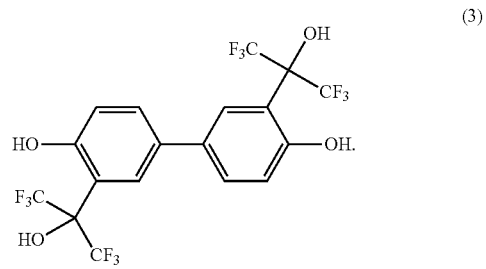
(3)

In the present invention, it is feasible to form an aromatic polyester polymer by mixing the fluorine-containing polymerizable monomer of Inventive Aspects 1 to 3 with a specific compound (any of compounds of the general formulas (4) to (6)) and reacting the resulting composition in such a manner as to perform condensation polymerization of the compound of the general formula (4), (5) or (6) to hydroxy group directly bonded to the aromatic ring of the fluorine-containing polymerizable monomer of Inventive Aspects 1 to 3. In this way, the HFIP-containing aromatic polyester is obtained as a polymer compound (any of compounds of the general formulas (7) to (12)) according to the present invention.

[Inventive Aspect 4]

A composition comprising:
the fluorine-containing polymerizable monomer according to any one of Inventive Aspects 1 to 3; and
at least one kind of compound selected from the group consisting of those of the general formulas (4), (5) and (6):

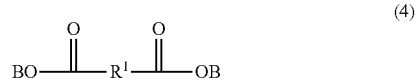
(4)

where $R^1$ represents an alkylene group or a divalent organic group obtained by elimination of two hydrogen atoms from an aromatic ring or an alicyclic ring; $R^1$ may contain an oxygen atom, a sulfur atom or a nitrogen atom in its structure, and may have a part of hydrogen atoms substituted with a fluorine atom, a chlorine atom, an alkyl group or a fluoroalkyl group; and B each independently represent a hydrogen atom, a $C_1$-$C_{10}$ alkyl group or a $C_6$-$C_{10}$ aryl group;

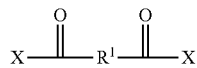
(5)

where $R^1$ represents an alkylene group or a divalent organic group obtained by elimination of two hydrogen atoms from an aromatic ring or an alicyclic ring; $R^1$ may contain an oxygen atom, a sulfur atom or a nitrogen atom in its structure, and may have a part of hydrogen atoms substituted with a fluorine atom, a chlorine atom, an alkyl group or a fluoroalkyl group; and X each independently represent a chlorine atom, a fluorine atom, a bromine atom or an iodine atom;

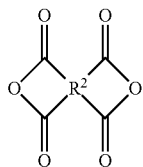
(6)

where $R^2$ represents a tetravalent organic group obtained by elimination of four hydrogen atoms from an alkane, an aromatic group or an alicyclic ring; $R^2$ may contain an oxygen atom, a sulfur atom or a nitrogen atom in its structure, and may have a part of hydrogen atoms substituted with a fluorine atom, a chlorine atom, an alkyl group or a fluoroalkyl group.

[Inventive Aspect 5]

A polymer compound having a repeating unit of the general formula (7):

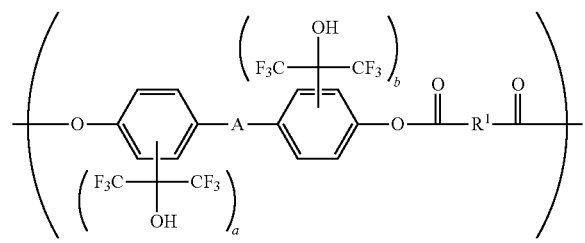
(7)

where A represents a single bond, an oxygen atom, a sulfur atom, $SO_2$, $CH_2$, $CO$, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorine; $R^1$ represents an alkylene group or a divalent organic group obtained by elimination of two hydrogen atoms from an aromatic ring or an alicyclic ring; $R^1$ may contain an oxygen atom, a sulfur atom or a nitrogen atom in its structure, and may have a part of hydrogen atoms substituted with a fluorine atom, a chlorine atom, an alkyl group or a fluoroalkyl group; and a and b each independently represent an integer of 0 to 2 and satisfy a relationship of $1 \le a+b \le 4$.

[Inventive Aspect 6]

The polymer compound according to Inventive Aspect 5, wherein the repeating unit of the general formula (7) is of the general formula (8):

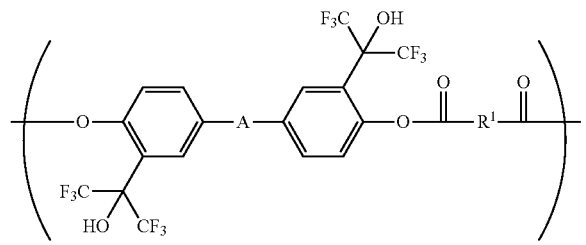
(8)

where A represents a single bond, an oxygen atom, a sulfur atom, $SO_2$, $CH_2$, $CO$, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorine; $R^1$ represents an alkylene group or a divalent organic group obtained by elimination of two hydrogen atoms from an aromatic ring or an alicyclic ring; and $R^1$ may contain an oxygen atom, a sulfur atom or a nitrogen atom in its structure, and may have a part of hydrogen atoms substituted with a fluorine atom, a chlorine atom, an alkyl group or a fluoroalkyl group.

[Inventive Aspect 7]

The polymer compound according to Inventive Aspect 6, wherein the repeating unit of the general formula (8) is of the formula (9):

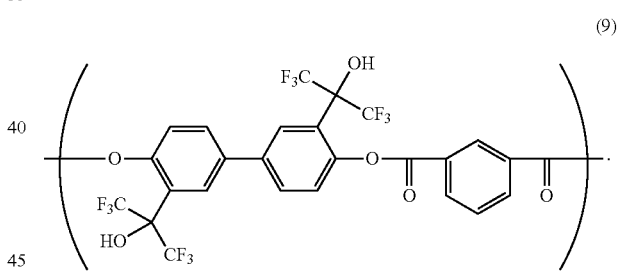
(9)

[Inventive Aspect 8]

A polymer compound having a repeating unit of the general formula (10):

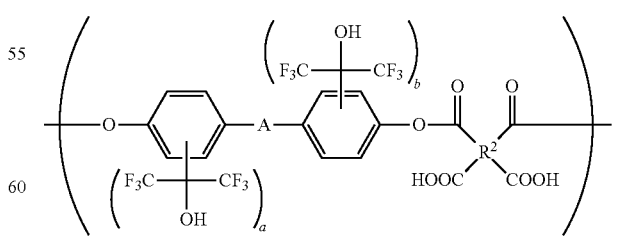
(10)

where A represents a single bond, an oxygen atom, a sulfur atom, $SO_2$, $CH_2$, $CO$, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorine; $R^2$ represents a tetravalent organic group obtained by elimination of four hydrogen atoms from an alkane, an aromatic group or an alicyclic ring; $R^2$ may contain an oxygen atom, a sulfur atom or a nitrogen atom in its structure, and may have a part of hydrogen atoms substituted with a fluorine atom, a chlorine atom, an alkyl group or a fluoroalkyl group; and a and b each independently represent an integer of 0 to 2 and satisfy a relationship of $1 \le a+b \le 4$.

[Inventive Aspect 9]

The polymer compound according to Inventive Aspect 8, wherein the repeating unit of the general formula (10) is of the general formula (11):

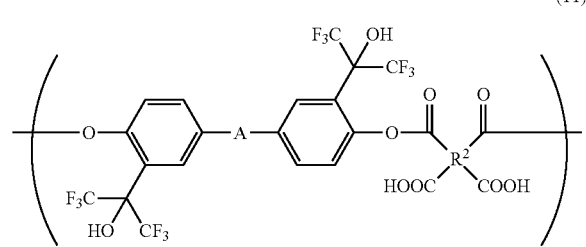

(11)

where A represents a single bond, an oxygen atom, a sulfur atom, $SO_2$, $CH_2$, CO, $C(CH_3)_2$, $C(CH_3)(CH_2CH_3)$, $C(CF_3)_2$, $C(CH_3)(C_6H_5)$, $CH_2$—$C_6H_4$—$CH_2$ or a divalent organic group obtained by elimination of two hydrogen atoms from benzene, biphenyl, naphtharene, cyclohexene or fluorine; $R^2$ represents a tetravalent organic group obtained by elimination of four hydrogen atoms from an alkane, an aromatic group or an alicyclic ring; and $R^2$ may contain an oxygen atom, a sulfur atom or a nitrogen atom in its structure, and may have a part of hydrogen atoms substituted with a fluorine atom, a chlorine atom, an alkyl group or a fluoroalkyl group.

[Inventive Aspect 10]

The polymer compound according to Inventive Aspect 9, wherein the repeating unit of the general formula (11) is of the general formula (12):

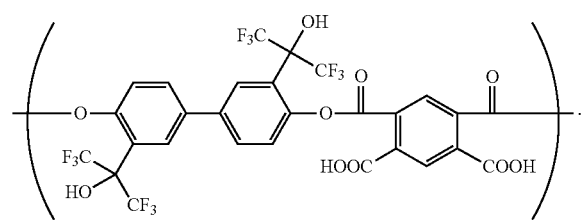

(12)

In each of the polymer compounds of Inventive Aspects 5 to 10, it is feasible to substitute a hydrogen atom of OH site of HFIP group with a glycidyl group. The thus-obtained polymer compound is, even alone, easily curable.

[Inventive Aspect 11]

The polymer compound according to any one of Inventive Aspects 5 to 10, wherein at least a part of hydrogen atoms of OH sites of 2-hydroxy-1,1,1,3,3,3-hexafluoroisopropyl groups is substituted with a glycidyl group.

It is further feasible to obtain a cured product by mixing the polymer compound of Inventive Aspects 5 to 10 with an epoxy compound and curing the resulting composition.

[Inventive Aspect 12]

A composition comprising:

the polymer compound according to any one of Inventive Aspects 5 to 10; and an epoxy compound.

[Inventive Aspect 13]

The composition according to Inventive Aspect 12, wherein the epoxy compound is of the general formula (13):

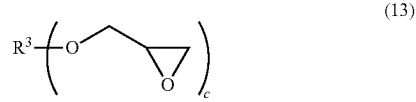

(13)

where c represents an integer of 1 to 4; $R^3$ represents an organic group obtained by elimination of c number of hydrogen atoms from an alkane, an aromatic ring or an alicyclic ring; and $R^3$ may contain an oxygen atom, a sulfur atom or a nitrogen atom in its structure, and may have a part of hydrogen atoms substituted with an alkyl group, a fluorine atom, a chlorine atom or a fluoroalkyl group.

[Inventive Aspect 14]

A cured product obtained by cross-linking of the glycidyl group of the polymer compound according to Inventive Aspect 11.

[Inventive Aspect 15]

A cured product obtained by cross-linking of the composition according to Inventive Aspect 12 or 13.

One example of the cured product of Inventive Aspect 14 or 15, which is obtained from the polymer compound of Inventive Aspect 11 or the composition of Inventive Aspect 12 or 13 by thermal curing etc., is a cured film formed by applying a coating of e.g. the composition to a substrate by a wet coating process and thermally curing/cross-linking the coating. This cured film is suitable for use as coatings for flat panel displays, protection films for substrates in electronic circuit boards, protection films for semiconductors and the like.

As mentioned above, it is possible according to the present invention to provide the novel fluorine-containing polymerizable monomer with the HFIP group for obtaining the material that combines adequate hydrophilicity with low water adsorption of fluorine-containing compound and to provide the aromatic polyester as the novel polymer compound using the fluorine-containing polymerizable monomer. The fluorine-containing aromatic polyester with the HFIP groups but no heterocyclic ring according to the present invention has much higher transparency as compared to conventional polyhydric aromatic polyesters with HFIP groups.

DETAILED DESCRIPTION OF THE EMBODIMENTS

1. Fluorine-containing Polymerizable Monomer

According to the present invention, there is provided a fluorine-containing polymerizable monomer of the general formula (1).

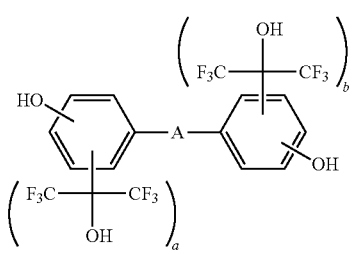

(1)

In the general formula (1), A represents a single bond, an oxygen atom, a sulfur atom, SO$_2$, CH$_2$, CO, C(CH$_3$)$_2$, C(CH$_3$)(CH$_2$CH$_3$), C(CF$_3$)$_2$, C(CH$_3$)(C$_6$H$_5$), CH$_2$—C$_6$H$_4$—CH$_2$ or a divalent organic group obtained by elimination of two hydrogen atoms from benzene, biphenyl, naphtharene, cyclohexene or fluorine; and a and b each independently represent an integer of 0 to 2 and satisfy a relationship of $1 \leq a+b \leq 4$.

The following are specific examples of the fluorine-containing polymerizable monomer of the general formula (1).

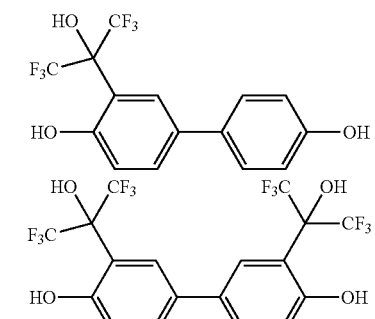

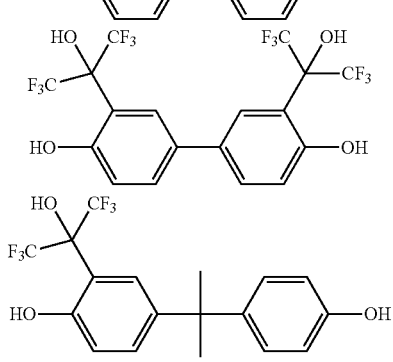

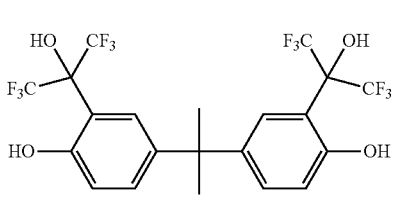

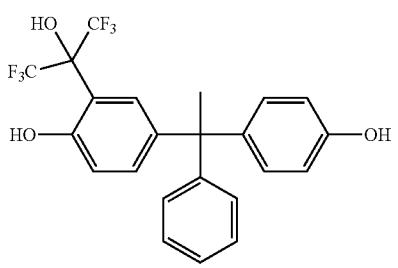

-continued

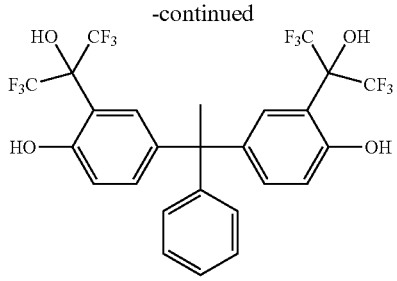

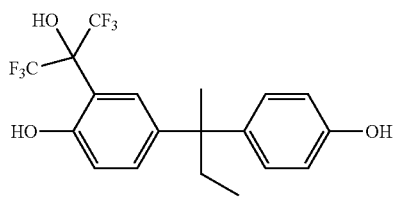

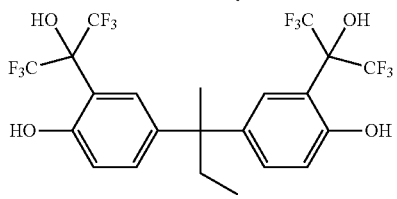

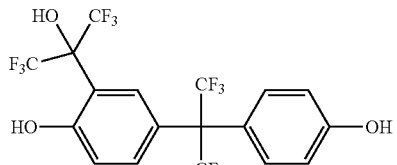

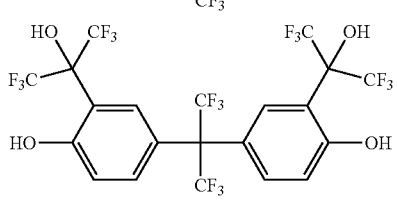

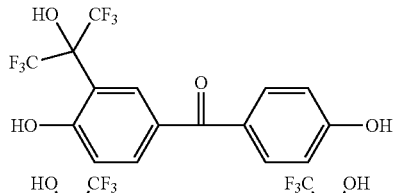

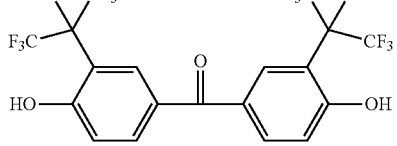

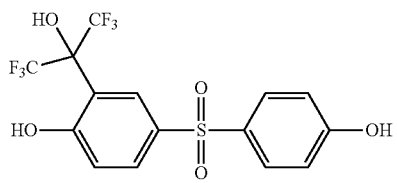

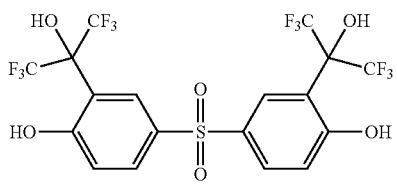

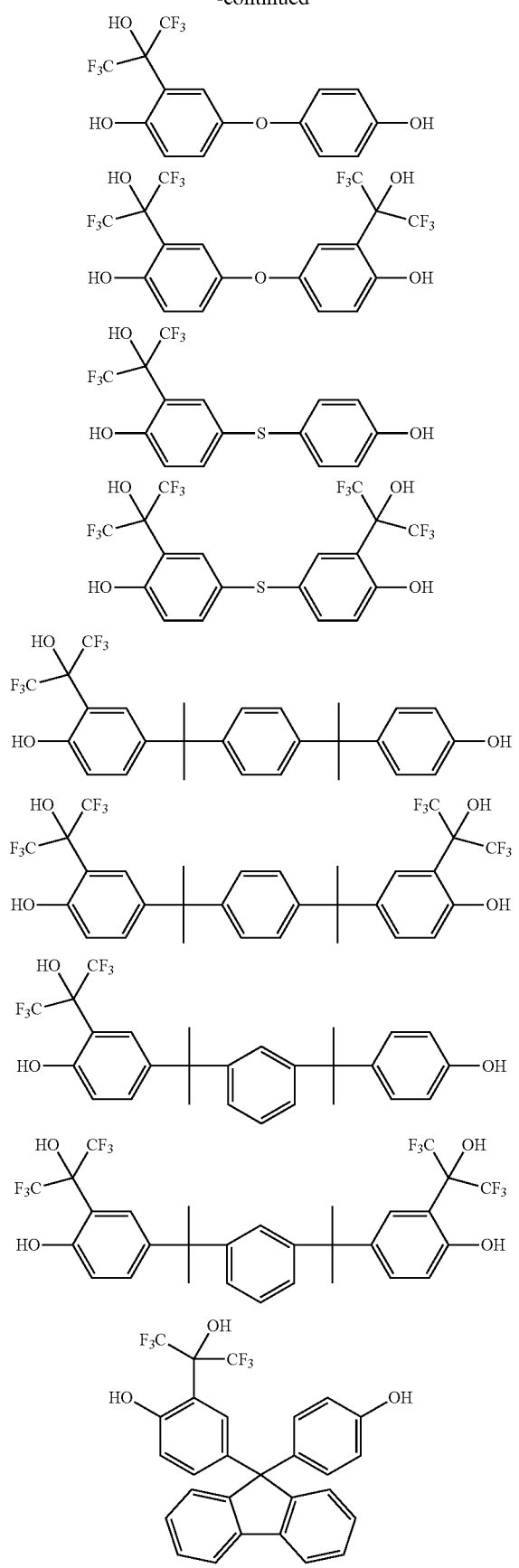
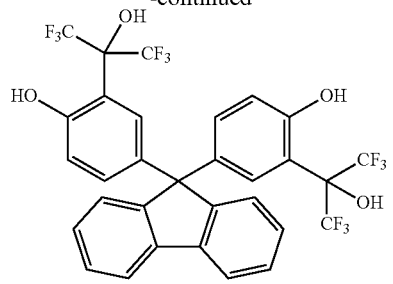
There can also be used fluorine-containing polymerizable monomers of the following formulas (a) to (j) synthesized from the fluorine-containing polymerizable monomer of the general formula (1). The fluorine-containing polymerizable monomers of the formulas (a) to (j) are herein also included in the scope of the present invention.
(a)
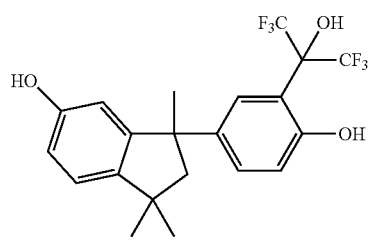
(b)
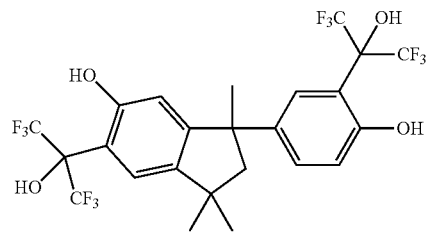
(c)
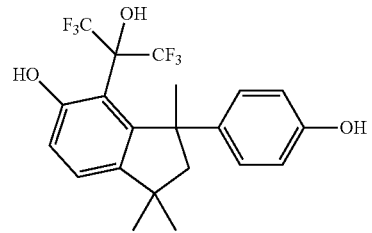
(d)
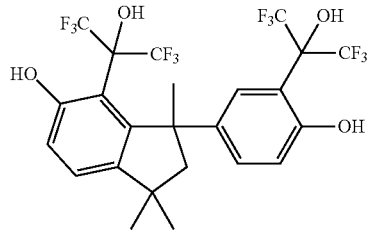
(e)
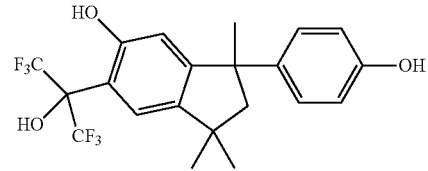

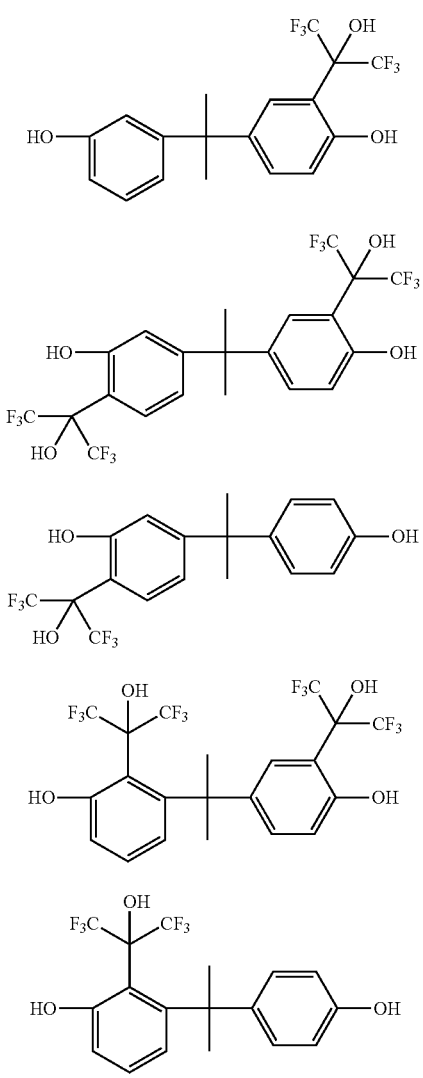

(f)
(g)
(h)
(i)
(j)

Among others, preferred as a raw material of polymers are those having two HFIP groups in terms the ease of synthesis thereof. Particularly preferred is a fluorine-containing polymerizable monomer of the formula (3).

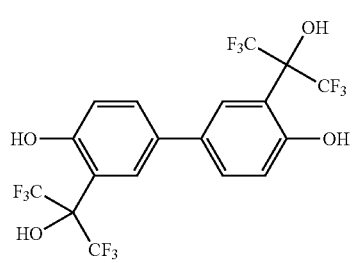

(3)

2. Synthesis of Fluorine-containing Polymerizable Monomer

Next, an explanation will be given of the method for synthesizing the fluorine-containing polymerizable monomer of the formula (3) by way of example.

The fluorine-containing polymerizable monomer of the formula (3) is a diol and is synthesized by reacting 4,4'-biphenol with hexafluoroacetone or hexafluoroacetone trihydrate.

As the boiling point of hexafluoroacetone is −28° C., it is preferable to perform the addition reaction of hexafluoroacetone to the 4,4'-biphenol with the use of a cooling device or a sealed reaction vessel, particularly preferably a sealed reaction vessel, for the purpose of maintaining hexafluoroacetone in the reaction system.

As the boiling point of hexafluoroacetone trihydrate is 105° C., hexafluoroacetone trihydrate is easier to handle than hexafluoroacetone. It is thus feasible to perform the addition reaction of hexafluoroacetone trihydrate to the 4,4'-biphenol under water cooling with the use of a reflux condenser, for the purpose of maintaining hexafluoroacetone trihydrate in the reaction system, although the addition reaction can be performed with the use of a sealed reaction vessel.

In this addition reaction, the amount of the hexafluoroacetone or hexafluoroacetone trihydrate used is generally 2.0 to 8.0 mol equivalent, preferably 2.2 to 3.0 mol equivalent, relative to the 4,4'-biphenol. When the amount of the hexafluoroacetone or hexafluoroacetone trihydrate is less than 2.0 mol equivalent, the fluorine-containing polymerizable monomer of the formula (3) is low in yield. The addition reaction proceeds when the hexafluoroacetone or hexafluoroacetone trihydrate is used in an amount exceeding 8.0 mol equivalent. It is not however necessary to use such a large amount of hexafluoroacetone or hexafluoroacetone trihydrate.

The addition reaction is generally preformed within a temperature range of 50 to 200° C., preferably 120 to 130° C. When the temperature is lower than 50° C., the addition reaction is unlikely to proceed. The fluorine-containing polymerizable monomer of the formula (3) is low in yield when the temperature is higher than 200° C., in particular 250° C. or higher.

Although the addition reaction proceeds without the use of a catalyst, it is feasible to promote the addition reaction with the use of an acid catalyst.

Examples of the acid catalyst are: Lewis acids such as aluminum chloride, iron (III) chloride and boron fluoride; organic sulfonic acids such as benzenesulfonic acid, camphorsulfonic acid (CSA), methanesulfonic acid, p-toluenesulfonic acid (pTsOH), p-toluenesulfonic acid (pTsOH) monohydrate and pyridinium p-toluenesulfonic acid (PPTS). Among others, aluminum chloride, iron (III) chloride, methanesulfonic acid and p-toluenesulfonic acid (pTsOH) monohydrate are preferred in view of the availability.

The amount of the catalyst used is generally 1 to 50 mol %, preferably 3 to 40 mol %, per 1 mol of the 4,4'-biphenol. When the amount of the catalyst used is less than 1 mol %, the fluorine-containing polymerizable monomer of the formula (3) is low in yield. The addition reaction proceeds when the catalyst is used in an amount exceeding 50 mol %. It is not however necessary to use such a large amount of catalyst.

The addition reaction can be preformed with or without the use of a solvent.

There is no particular limitation on the solvent as long as the solvent is not involved in the addition reaction. Preferred examples of the solvent are: aromatic hydrocarbon solvents such as xylene, toluene, benzene, anisole, diphenyl ether, nitrobenzene and benzonitrile; chlorinated solvents such as chloroform, methylene chloride, dichloroethane and dichlorobenzene; and water.

There is also no particular limitation on the amount of the solvent used. However, it is not favorable to use the solvent in a large amount because the use of a large amount of solvent leads to a deterioration in the yield of the fluorine-containing polymerizable monomer of the formula (3) per unit volume of the reaction vessel.

When the addition reaction is performed with the use of the sealed reaction vessel (autoclave), the process of the addition reaction varies depending on whether to use the hexafluoroacetone or hexafluoroacetone trihydrate. In the case of using the hexafluoroacetone, it is preferable to first place the 4,4'-biphenol and the catalyst or solvent in the reaction vessel, and then, add the hexafluoroacetone into the reaction vessel while heating the reaction vessel in such a manner that the pressure inside the reaction vessel does not exceed 0.5 MPa.

In the case of using the hexafluoroacetone trihydrate, it is feasible to perform the addition reaction by placing the 4,4'-biphenol and the hexafluoroacetone trihydrate in the reaction vessel and adding the catalyst or solvent into the reaction vessel.

In the addition reaction, there is no particular limitation on the reaction time. The reaction time is set as appropriate depending on the reaction temperature, the amount of the catalyst used etc. It is preferable to complete the addition reaction after confirming by ordinary analytical means such as gas chromatography that the raw material has sufficiently been consumed.

After the completion of the addition reaction, the fluorine-containing polymerizable monomer of the formula (3) can be obtained by extraction, distillation, crystallization etc. Further, the fluorine-containing polymerizable monomer of the formula (3) can be purified by column chromatography, recrystallization etc. as needed.

3. Composition and Polymer Compound

According to the present invention, there is also provided a polymer compound by condensation polymerization of a composition containing the fluorine-containing polymerizable monomer of the general formula (1) or (2) or the formula (3). The fluorine-containing polymerizable monomer has two hydroxy groups and at least one HFIP group and thus contains two or more hydroxy groups in its molecule. In the production of the polymer compound, it is preferable to react a hydroxy group(s) bonded to the aromatic ring(s) of the fluorine-containing polymerizable monomer.

More specifically, the polymer compound is formed with a repeating unit of the general formula (7) or (8), the formula (9), the general formula (10) or (11) or the formula (12) by mixing the fluorine-containing polymerizable monomer with at least one selected from compounds of the general formulas (4) to (6), and then, subjecting the resulting composition to condensation polymerization under predetermined reaction conditions e.g. suitable temperature range in the present invention.

3.1. Composition of Fluorine-Containing Polymerizable Monomer and Compound of General Formula (4) or (5) and Polymer Compound Obtained Therefrom The polymer compound having the repeating unit of the general formula (7) or (8) or the formula (9) is obtained when the composition containing the fluorine-containing polymerizable monomer of the general formula (1) or (2) or the formula (3) and the compound of general formula (4) or (5) is subjected to condensation polymerization under predetermined reaction conditions. After that, a hydrogen atom of the HFIP group may be substituted with a glycidyl group as needed.

[Compound of General Formula (4)]

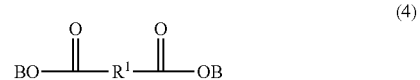

In the general formula (4), $R^1$ represents an alkylene group or a divalent organic group obtained by elimination of two hydrogen atoms from an aromatic ring or an alicyclic ring; $R^1$ may contain an oxygen atom, a sulfur atom or a nitrogen atom in its structure, and may have a part of hydrogen atoms substituted with a fluorine atom, a chlorine atom, an alkyl group or a fluoroalkyl group; and B each independently represent a hydrogen atom, a $C_1$-$C_{10}$ alkyl group or a $C_6$-$C_{10}$ aryl group.

[Compound of General Formula (5)]

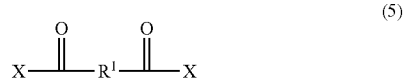

In the general formula (5), $R^1$ represents an alkylene group or a divalent organic group obtained by elimination of two hydrogen atoms from an aromatic ring or an alicyclic ring; $R^1$ may contain an oxygen atom, a sulfur atom or a nitrogen atom in its structure, and may have a part of hydrogen atoms substituted with a fluorine atom, a chlorine atom, an alkyl group or a fluoroalkyl group; and X each independently represent a chlorine atom, a fluorine atom, a bromine atom or an iodine atom.

As a raw material of the compound of the general formula (4) or (5), there can be used either an aliphatic carboxylic acid or an aromatic carboxylic acid.

Example of the aliphatic carboxylic acid are oxalic acid, malonic acid, succinic acid, glutaric acid, adipic acid, pimelic acid, suberic acid, azelaic acid and sebacic acid.

Examples of the aromatic carboxylic add are phthalic acid, isophthalic acid, telephthalic acid, 3,3'-dicarboxylic diphenyl ether, 3,4'-dicarboxylic diphenyl ether, 4,4'-dicarboxylic diphenyl ether, 3,3'-dicarboxylic diphenylmethane, 3,4'-dicarboxylic diphenylmethane, 4,4'-dicarboxylic diphenylmethane, 3,3'-dicarboxylic diphenyl difluoromethane, 3,4'-dicarboxylic diphenyldifluoromethane, 4,4'-dicarboxylic diphenyldifluoromethane, 3,3'-dicarboxylic diphenyl sulfone, 3,4'-dicarboxylic diphenyl sulfone, 4,4' -dicarboxylic diphenyl sulfone, 3,3'-dicarboxylic diphenyl sulfide, 3,4'-dicarboxylic diphenyl sulfide, 4,4'-dicarboxylic diphenyl sulfide, 3,3'-dicarboxylic diphenyl ketone, 3,4'-dicarboxylic diphenyl ketone, 4,4'-dicarboxylic diphenyl ketone, 2,2-bis(3-carboxyphenyl)propane, 2,2-bis(3,4'-carboxyphenyl)propane, 2,2-bis(4-carboxyphenyl)propane, 2,2-bis(3-carboxyphenyl)hexafluoropropane, 2,2-bis(3,4'-carboxyphenyl)hexafluoropropane, 2,2-bis(4-carboxyphenyl) hexafluoropropane, 1,3-bis(3-carboxyphenoxy)benzene, 1,4-bis(3-carboxyphenoxy)benzene, 1,4-bis(4-carboxyphenoxy)benzene, 3,3'-(1,4-phenylenebis(1-methylethylidene)) bis(benzoic acid), 3,4'-(1,4-phenylenebis(1-methylethylidene))bis(benzoic acid), 4,4'-(1,4-phenylenbis(1-methylethylidene))bis(benzoic add), 2,2-bis(4-(3-carboxyphenoxy)phenyl)propane, 2,2-bis(4-(4-carboxyphenoxy)phenyl)propane, 2,2-bis(4-(3-carboxyphenoxy)phenyl)hexafluoropropane, 2,2-bis(4-(4-carboxyphenoxy)phenyl)hexafluoropropane, bis(4-(3-carboxyphenoxy)phenyl)sulfide, bis(4-(4-carboxyphenoxy) phenyl)sulfide, bis(4-(3-carboxyphenoxy)phenyl)sulfone, bis(4-(4-carboxyphenoxy)phenyl)sulfone, perfluorononenyloxy group-containing carboxylic adds such as 5-(perfluorononenyloxy)isophthalic acid, 4-(perfluorononenyloxy)terephthalic acid, 2-(perfluorononenyloxy)terephthalic acid and 4-methoxy-5-(perfluorononenyloxy)isophthalic acid and perfluorohexenyloxy group-containing carboxylic acids such as 5-(perfluorohexenyloxy)isophthalic acid, 4-(perfluorohexenyloxy)phthalic acid, 2-(perfluorohexenyloxy)terephthalic acid and 4-methoxy-5-(perfluorohexenyloxy)isophthalic acid. Among others, isophthalic acid is preferred in view of the ease of condensation polymerization thereof and the transparency of the resulting polymer compound.

As mentioned above, the polymer compound having the repeating unit of the general formula (7) or (8) or the formula (9) is obtained by reacting the fluorine-containing polymerizable monomer of the general formula (1) or (2) or the formula (3) with the compound of the general formula (4) or (5).

There is no particular limitation on the method and conditions of the polymerization reaction. It is feasible to perform the condensation polymerization by melting the composition of the fluorine-containing polymerizable monomer and the compound of the general formula (4) or (5) at a temperature of 150° C. or higher in the absence of a solvent. It is alternatively feasible to perform the condensation polymerization in an organic solvent at a temperature of preferably 150° C. or higher or in an organic solvent at a temperature of 20 to 80° C.

There is no particular limitation on the organic solvent as long as both of the raw material components can be dissolved in the organic solvent. Examples of the organic solvent are: amide solvents such as N,N-dimethylformamide, N,N-dimethylacetamide, N-methylformamide, hexamethylphosphoric triamide and N-methyl-2-pyrrolidone; aromatic solvents such as benzene, anisole, diphenyl ether, nitrobenzene and benzonitrile; halogenated solvents such as chloroform, dichloromethane, 1,2-dichloroethane and 1,1,2,2-tetrachloroethane; lactone compounds such as γ-butyrolactone, γ-valerolactone, δ-valerolactone, γ-caprolactone, ε-caprolactone and α-methyl-γ-butyrolactone. These organic solvents can be used solely or in the form of a mixture of two or more kinds thereof. It is effective to perform the polymerization reaction in the coexistence of an acid receptor such as pyridine or triethylamine with the organic solvent.

After that, a hydrogen atom of the HFIP group may be substituted with a glycidyl group as needed. In this substitution reaction, it is feasible to obtain the target glycidyl substituted product by reacting the HFIP group with epichlorohydrin in the presence of an alkali metal compound (see Non-Patent Document 3).

Examples of the alkali metal compound are: alkali metal hydroxides such as sodium hydroxide, lithium hydroxide and potassium hydroxide; alkali metal salts such as sodium carbonate, sodium hydrogen carbonate, sodium chloride, lithium chloride and calcium chloride; alkali metal alkoxides such as sodium methoxide and sodium ethoxide; alkali metal phenoxides; sodium hydride; lithium hydride; and alkali metal salts of organic acids, such as sodium acetate and sodium stearate.

The substitution reaction may be performed with the use of a phase transfer catalyst. As the phase transfer catalyst, there can suitably be used a quaternaty ammonium salt. Examples of the quaternaty ammonium salt are tetramethylammonium chloride, tetramethylammonium bromide, tetramethylammonium hydroxide, triethylmethylammonium chloride, tetraethylammonium chloride, tetraethylammonium bromide, tetrabutylammonium chloride, tetrabutylammonium bromide, tetrabutylammonium iodide, benzyltrimethylammonium chloride, benzyltrimethylammonium bromide, benzyltrimethylammonium hydroxide, benzyltributylammonium chloride and phenyltrimethylammonium chloride.

Alternatively, a hydrogen atom of the HFIP group may be substituted with a glycidyl group by protecting the HFIP group with an allyl group, and then, oxidizing a double bond of the allyl protection product. More specifically, it is feasible to obtain the target glycidyl substituted product by reacting the HFIP group with an allyl halide such as allyl chloride, allyl bromide or allyl iodide, and then, reacting the resulting allyl protection product with an oxidizing agent such as hydrogen peroxide or alkyl hydroperoxide.

3.2. Composition of Fluorine-Containing Polymerizable Monomer and Compound of General Formula (6) and Polymer Compound Obtained Therefrom The polymer compound having the repeating unit of the general formula (10) or (11) or the formula (12) is obtained when the composition containing the fluorine-containing polymerizable monomer of the general formula (1) or (2) or the formula (3) and the compound of general formula (6) is subjected to condensation polymerization under predetermined reaction conditions. After that, a hydrogen atom of the HFIP group may be substituted with a glycidyl group as needed.

[Compound of General Formula (6)]

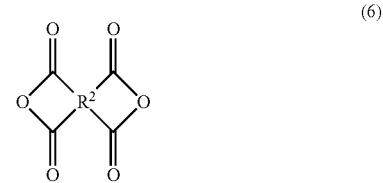

(6)

In the general formula (6), $R^2$ represents a tetravalent organic group obtained by elimination of four hydrogen atoms from an alkane, an aromatic group or an alicyclic ring; $R^2$ may contain an oxygen atom, a sulfur atom or a nitrogen atom in its structure, and may have a part of hydrogen atoms substituted with a fluorine atom, a chlorine atom, an alkyl group or a fluoroalkyl group.

The compound of the general formula (6) can be a tetracarboxylic dianhydride commonly used as a raw material of polyamic acids and polyimides.

Examples of the tetracarboxylic dianhydride are benzenetetracarboxylic dianhydride (pyromellitic dianhydride; PMDA), trifluoromethylbenzenetetracarboxylic dianhydride, bistrifluoromethylbenzenetetracarboxylic dianhydride, difluorobenzenetetracarboxylic dianhydride, naphthalenetetracarboxylic dianhydride, biphenyltetracarboxylic dianhydride, terphenyltetracarboxylic dianhydride, hexafluoroisopropylidenediphthalic dianhydride, oxydiphthalic dianhydride, bicycle(2,2,2)oct-7-ene-2,3,4,5-tetracarboxylic dianhydride, 2,2-bis(3,4-dicarboxyphenyl)hexafluoropropionic dianhydride (6FDA), 2,3,4,5-thiophenetetracarboxylic dianhydride, 2,5,6,2',5',6'-hexafluoro-3,3',4,4'-biphenyltetracarboxylic dianhydride, bis(3,4-dicarboxyphenyl)sulfonic dianhydride and 3,4,9,10-perylenetetracarboxylic dianhydride. Among others, benzenetetracarboxylic dianhydride (pyromellitic dianhydride; PMDA) is preferred in view of the availability and ease of condensation polymerization thereof and the transparency of the resulting polymer compound.

As mentioned above, the polymer compound having the repeating unit of the general formula (10) or (11) or the formula (12) is obtained by condensation polymerization of the fluorine-containing polymerizable monomer of the general formula (1) or (2) or the formula (3) with the compound of the general formula (16).

In this condensation polymerization reaction, there can suitably be adopted the above-mentioned method and conditions of the polymerization reaction between the fluorine-containing polymerizable monomer and the compound of the general formula (4) or (5).

There is no particular limitation on the organic solvent as long as both of the raw material components can be dissolved in the organic solvent. Examples of the organic solvent are the same as above, including: amide solvents such as N,N-dimethylformamide, N,N-dimethylacetamide, N-methylformamide, hexamethylphosphoric triamide and N-methyl-2-pyrrolidone; aromatic solvents such as benzene, anisole, diphenyl ether, nitrobenzene and benzonitrile; halogenated solvents such as chloroform, dichloromethane, 1,2-dichloroethane and 1,1,2,2-tetrachloroethane; lactone compounds such as γ-butyrolactone, γ-valerolactone, δ-valerolactone, γ-caprolactone, ε-caprolactone and α-methyl-γ-butyrolactone. These organic solvents can be used solely or in the form of a mixture of two or more kinds thereof. It is effective to perform the polymerization reaction in the coexistence of an acid receptor such as pyridine or triethylamine with the organic solvent.

After that, a hydrogen atom of HFIP group may be substituted with a glycidyl group as needed. In this substitution reaction, it is feasible to obtain the target glycidyl substituted product by reacting the HFIP group with epichlorohydrin in the presence of an alkali metal compound in the same manner as above (see Non-Patent Document 3).

3.3. Diol Compound

In the production of the polymer compound having the repeating unit of the general formula (7) or (8), the formula (9), the general formula (10) or (11) or the formula (12), any other diol compound may be added as a copolymerization component to the fluorine-containing polymerizable monomer of the general formula (1) or (2) or the formula (3) and the compound of the general formula (4), (5) or (6) in order to impart desired heat resistance, solvent solubility etc. to the polymer compound.

Examples of the other diol compound are 1,4-cyclohexanediol, 1,3-adamantanediol, catechol, 1,3-benzenediol, 2,2'-dihydroxybiphenyl, 4,4'-dihydroxybiphenyl, 2,2'-methylenediphenol, 4,4'-methylenediphenol, ethylene glycol, propylene glycol, 2,2-bis(4-hydroxyphenyl)propane, 2,2-bis(4-hydroxyphenyl)-3-methylpropane, 2,2-bis(4-hydroxyphenyl)butane, 3,3-bis(4-hydroxyphenyl)pentane, 2,2-bis(4-hydroxyphenyl)-4-methylpentane, 3,3-bis(4-hydroxyphenyl)hexane, 2,2-bis(3-chloro-4-hydroxyphenyl)propane, 2,2-bis(3,5-dichloro-4-hydroxyphenyl)propane, 2,2-bis(3-bromo-4-hydroxyphenyl)propane, 2,2-bis(3,5-dibromo-4-hydroxyphenyl)propane, 2,2-bis(3-methyl-4-hydroxyphenyl)propane, 2,2-bis(4-hydroxyphenyl)-1,1,1,3,3,3-hexafluoropropane, 2,6-dihydroxynaphthalene, 2,3-dihydroxynaphthalene, 2,7-dihydroxynaphthalene, 1,4-dihydroxynaphthalene, 1,5-dihydroxynaphthalene, 2,3-dihydroxypyridine, 2,4-dihydroxypyridine, 4,4'-dihydroxydiphenyl ether, 4,4'-dihydroxydiphenyl sulfide, 4,4'-dihydroxydiphenyl suit 4,4'-dihydroxydiphenyl sulfone and 4,4'-dihydroxybenzophenone, Curing of Polymer Compound The polymer compound having the repeating unit of the general formula (7) or (8), the formula (9), the general formula (10) or (11) or the formula (12), i.e., polyester is usable as a varnish by dissolving the polymer compound in an organic solvent, a powder, a film or the like. Depending on the purpose of use of the polymer compound, any of an oxidation stabilizer, a filler, a silane coupling agent, a photosensitizer, a photopolymerization initiator and a sensitizer can be added to the polymer compound. In the case of the polymer compound as the varnish, the varnish of the polymer compound can be applied to a substrate of glass, silicon wafer, metal, metal oxide, ceramic material or resin by any known process such as spin coating, spray coating, flow coating, immersion coating or brush coating.

For improvement in transparency, heat resistance etc., it is feasible to mix the polymer compound having the repeating unit of the general formula (7) or (8), the formula (9), the general formula (10) or (11) or the formula (12) with an epoxy compound and cure the resulting polymer mixture by heating or light irradiation.

Examples of the epoxy compound are those obtained, as epoxy modification products, by contact of phenol novolac resin, cresol novolac resin, aromatic hydrocarbon formaldehyde-modified phenol resin, dicyclopentadiene-modified phenol resin, phenol aralkyl resin, cresol aralkyl resin, naphthol aralkyl resin, biphenyl-modified phenol aralkyl resin, phenol trimethylol methane resin, tetraphenylol ethane resin, naphthol novolac resin, naphthol phenol condensation novolac resin, biphenyl-modified phenol resin and aminotriazine-modified phenol resin with epichlorohydrin.

These epoxy compounds are commercially available. For example, there can be used: bisphenol A type epoxy resins available under the tradename of "EPICLON 840" from Dainippon Ink and Chemicals Inc. and "JER 828" from Mitsubishi Chemical Corporation; bisphanol F type epoxy resins available under the tradename of "ADEKA RESIN EP-4901" from Asahi Denka Corporation; cresol novolac type epoxy resins available under the tradename of "EPICLON N-600 series" from Dainippon Ink and Chemicals Inc.; dicyclopentadiene type epoxy resins available under the tradename of "EPICLON HP-7200 series" from Dainippon Ink and Chemicals Inc.; and triazine type epoxy resins available under the trade name of "TEPIC series" from Nissan Chemical Industries, Ltd.

The epoxy compound is preferably of the general formula (13) and is synthesized from a corresponding alcohol and epichlorohydrin.

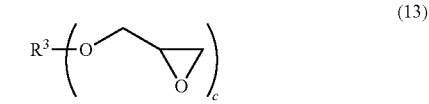

(13)

In the general formula (13), $R^3$ represents a monovalent organic group obtained by elimination of one hydrogen atom from an alkane, an aromatic ring or an alicyclic ring; $R^3$ may contain an oxygen atom, a sulfur atom or a nitrogen atom in its structure, and may have a part of hydrogen atoms substituted with an alkyl group, a fluorine atom, a chlorine atom or a fluoroalkyl group; and c represents an integer of 1 to 4.

Examples of the alcohol are 1,4-cyclohexanediol, 1,3-adamantanediol, catechol, 1,3-benzenediol, 2,2'-dihydroxybiphenyl, 4,4'-dihydroxybiphenyl, 2,2'-methylenediphenol, 4,4'-methylenediphenol, ethylene glycol, propylene glycol, 2,2-bis(4-hydroxyphenyl)propane, 2,2-bis(4-hydroxyphenyl)-3-methylpropane, 2,2-bis(4-hydroxyphenyl)butane, 3,3-bis(4-hydroxyphenyl)pentane, 2,2-bis(4-hydroxyphenyl)-4-methylpentane, 3,3-bis(4-hydroxyphenyl)hexane, 2,2-bis(3-chloro-4-hydroxyphenyl)propane, 2,2-bis(3,5-dichloro-4-hydroxyphenyl)propane, 2,2-bis(3-bromo-4-hydroxyphenyl)propane, 2,2-bis(3,5-dibromo-4-hydroxyphenyl)propane, 2,2-bis(3-methyl-4-hydroxyphenyl)propane, 2,2-bis(4-hydroxyphenyl)-1,1,1,3,3,3-hexafluoropropane, 2,6-dihydroxynaphthalene, 2,3-dihydroxynaphthalene, 2,7-dihydroxynaphthalene, 1,4-dihydroxynaphthalene, 1,5-dihydroxynaphthalene, 2,3-dihydroxypyridine, 2,4-dihydroxypyridine, 4,4'-dihydroxydiphenyl ether, 4,4'-dihydroxydiphenyl sulfide, 4,4'-dihydroxydiphenyl sulfoxide, 4,4'-dihydroxydiphenyl sulfone, 4,4'-dihydroxybenzophenone, 1,4-dihydroxyhexane, 2,2-bis(4-hydroxycyclohexyl)propane, 1,1'-methylene-di-2-naphthol, 4,4',4"-trihydroxytriphenylmethane, 1,1,1-tris(4-hydroxyphenyl)ethane and α,α',α"-tris(4-hydroxyphenyl)-1-ethyl-4-isopropylbenzene.

In the production of the cured product, an epoxy resin curing agent may be used in combination with the epoxy compound.

As the curing agent, there can be used an amine-based compound, an acid anhydride compound, an amide-based compound, a phenolic compound, a mercaptan-based compound, an imidazole-based compound, a polysulfide-based compound or a phosphorus compound. Specific examples of the curing agent are: thermal curing agents such as diaminodiphenylmethane, diaminodiphenylsulfone, diethylenetriamine, triethylenetetramine, polyalkylene glycol polyamine, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, 2-methylimidazole, triphenylphosphine, 2-ethyl-4-methylimidazole, BF3-amine complex and guanidine derivatives; and ultraviolet curing agents such as diphenyliodonium hexafluorophosphate and triphenylsulfonium hexafluorophosphate.

The mixing ratio of the polymer compound having the repeating unit of the general formula (7) or (8), the formula (9), the general formula (10) or (11) or the formula (12) and the epoxy compound are generally 10:90 to 90:10, preferably 30:70 to 70:30, more preferably 40:60 to 60:40, in units of mass ratio.

The mixing ratio of the epoxy compound and the epoxy resin curing agent is generally 70:30 to 99:1 in units of mass ratio.

It is feasible to form a cross-linked cured film by dissolving the composition in an organic solvent, forming a coating of the resulting solution on a glass or silicon substrate, and then, curing the coating by heating or by ultraviolet irradiation with the use of an ultraviolet (UV) lamp.

There is no particular limitation on the organic solvent as long as the composition can be dissolved in the organic solvent. Examples of the organic solvent are: amide solvents such as N,N-dimethylformamide, N,N-dimethylacetamide, N-methylformamide, hexamethylphosphoric triamide and N-methyl-2-pyrrolidone; cyclohexanone; propylene glycol monomethylether acetate; and γ-butyrolactone.

The cured film is formed by the wet film forming method, i.e., by applying the coating of the solution to the substrate and curing the coating and is thus suitable for use as coatings for flat panel displays, protection films for substrates in electronic circuit boards, protection films for semiconductors and the like.

EXAMPLES

The present invention will be described in more detail below by way of the following examples. It should be noted that the following examples are illustrative and are not intended to limit the present invention thereto.

In the following examples, identification of fluorine-containing monomers and property evaluation of polymer compounds were conducted by the following methods (1) to (6).

(1) NMR (Nuclear Magnetic Resonance) Measurement $^1$H-NMR and $^{19}$F-NMR were measured with a nuclear magnetic resonance spectrometer of 400 MHz resonance frequency (manufactured by Nihon Electronics Co., Ltd.).

(2) DI-MS (Mass Spectrum) Measurements

Mass spectrum was measured with a mass spectrometer (model "JMS-T100GC" manufactured by Nihon Electronics Co., Ltd.).

(3) Molecular Weight Determination

Molecular weight was determined in terms of polystyrene by gel permeation chromatography (GPC) using tetrahydrofuran (abbreviated as "THF").

(4) Solubility Evaluation

Solubility evaluation was performed by adding the polymer in N-methylpyrrolidone (abbreviated as "NMP"), cyclohexanone or 2.38 mass % tetramethylammonium hydroxide (abbreviated as "TMAH) solution in such a manner that the polymer resin concentration of the resulting solution was 10 mass %, stirring the solution for 1 hour at room temperature, and then, visually checking the presence or absence of the polymer solute. Herein, each of NMP and cyclohexanone is a polar solvent; and TMAH is a strong alkali solution used as a surface treatment agent for semiconductors or a photoresist developer for lithography processes.

(5) Light Transmittance Measurements

Light transmittance measurements were made with an ultraviolet and visible spectrophotometer (model "UV-3150" manufactured by Shimadzu Corporation).

(6) Residual Film Ratio Determination

Residual film ratio was determined according the following equation: (film thickness after heating/film thickness before heating)×100 by measuring the thickness of the film before and after heating with a needle-contact type surface profile tester (model "Dektak8" manufactured by U.S. Deeco Inc.).

[Synthesis of Fluorine-Containing Polymerizable Monomers]

Example 1

Synthesis of Fluorine-containing Polymerizable Monomer of Formula (3)

As indicated in the following reaction scheme, a fluorine-containing polymerizable monomer of the formula (3), i.e., 3,3-bis(1,1,1,3,3,3-hexafluoro-2-hydroxypropane-2-yl)-4,4-biphenol was synthesized by reaction of 4,4'-biphenol (A) with hexafluoroacetone.

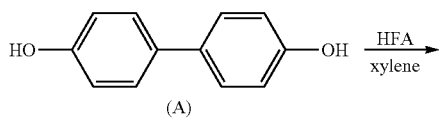

(A)

-continued

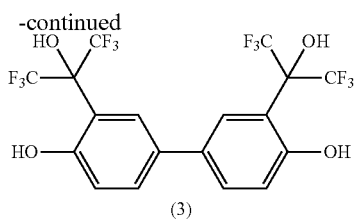

(3)

Under room temperature 2° C.), 250 g of xylene was placed in a stainless autoclave, followed by adding thereto 100 g (0.54 mol) of 4,4'-biphenol (A), 1 g of $CH_3SO_3H$ and then 196 g (1.18 mol) of hexafluoroacetone. The temperature of the autoclave was gradually raised and maintained at 100° C. In this state, the mixture inside the autoclave was reacted by stirring for 8 hours.

The reaction product containing the raw material inside the reaction system was filtrated. The filtration residue was dissolved in isopropyl ether and washed with water. The resulting organic phase was subjected to dehydration with the addition of anhydrous magnesium sulfate, and then, distilled under a reduced pressure to remove therefrom isopropyl ether. With the addition of hexane as a poor solvent to the distillation residue, the fluorine-containing polymerizable monomer of the formula (3) was precipitated and thereby obtained at a yield of 76%.

The analysis results of the fluorine-containing polymerizable monomer of the formula (3) are indicated below $^1$H-NMR (solvent: d-DMSO, TMS) δ: 10.8 (1H, s), 8.6 (1H, s), 7.7 (1H, s), 7.5 (1H, dd, J=8.6 Hz), 7.0 (1H, d, J=8.3 Hz)
$^{19}$F-NMR (solvent: d-DMSO, $CCl_3F$) δ: −72.8 (12F, s)
DI-MS (FD+): m/z 518.06 (M+)

Example 2

Synthesis of Fluorine-containing Polymerizable Monomers of Formulas (D) and (D)

As indicated in the following reaction scheme, a fluorine-containing polymerizable monomer of the formula (C) or (D) was synthesized by reaction of a compound (B) with hexafluoroacetone,

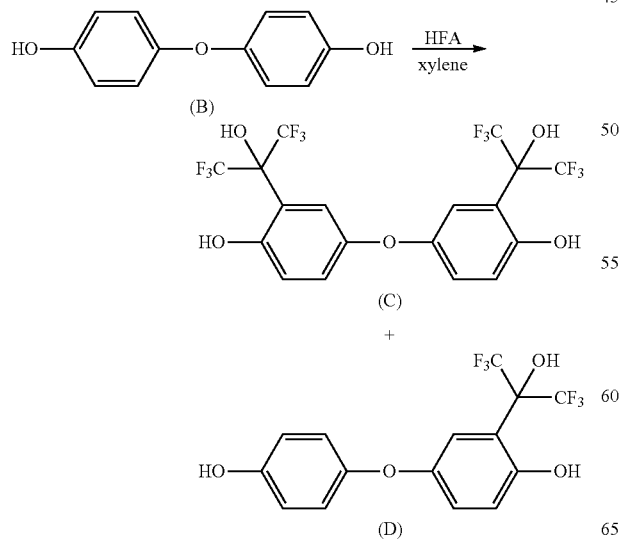

Under room temperature (20° C.), 150 g of xylene was placed in a stainless autoclave, followed by adding thereto 25 g (0.16 mol) of the compound (B), 0.25 g of $CH_3SO_3H$ and then 57 g (0.34 mol) of hexafluoroacetone. The temperature of the autoclave was gradually raised and maintained at 100° C. In this state, the mixture inside the autoclave was reacted by stirring for 8 hours.

The reaction product containing the raw material inside the reaction system was filtrated. The filtration residue was dissolved in isopropyl ether and washed with water. The resulting organic phase was subjected to dehydration with the addition of anhydrous magnesium sulfate, and then, distilled under a reduced pressure to remove therefrom isopropyl ether. With the addition of hexane as a poor solvent to the distillation residue, the fluorine-containing polymerizable monomer was precipitated. It was confirmed by DI-MS analysis that the solid precipitate was a mixture of the fluorine-containing polymerizable monomer of the formula (D) (HFIP-monosubstituted product) and the fluorine-containing polymerizable monomer of the formula (C) (HFIP-disubstituted product) at a ratio of C:D=2:3.

The analysis results of the fluorine-containing polymerizable monomer of the formula (C) are indicated below.
DI-MS (FD+): m/z 534.05 (M+), 368.51 (M+)

Example 3

Synthesis of Fluorine-containing Polymerizable Monomers of Formulas (F) and (G)

As indicated in the following reaction scheme, a fluorine-containing polymerizable monomer of the formula (F) or (G) was synthesized by reaction of a compound (E) with hexafluoroacetone.

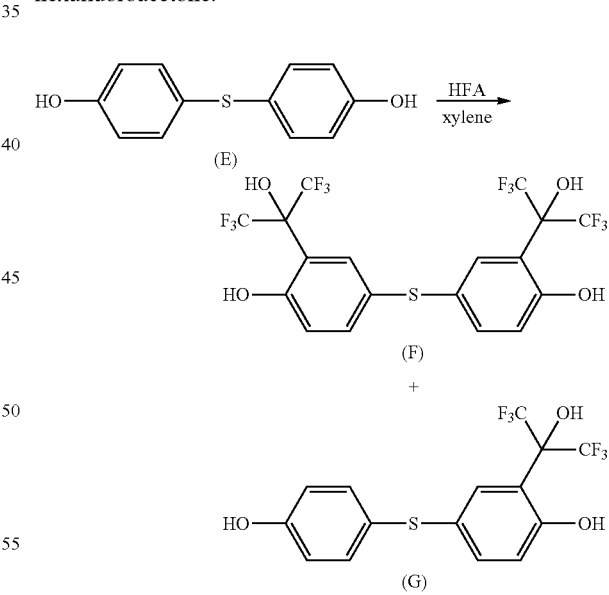

Under room temperature (20° C.), 150 g of xylene was placed in a stainless autoclave, followed by adding thereto 25 g (0.16 mol) of the compound (E), 0.25 g of $CH_3SO_3H$ and then 57 g (0.34 mol) of hexafluoroacetone. The temperature of the autoclave was gradually raised and maintained at 100° C. In this state, the mixture inside the autoclave was reacted by stirring for 8 hours.

The reaction product containing the raw material inside the reaction system was filtrated. The filtration residue was dissolved in isopropyl ether and washed with water. The resulting organic phase was subjected to dehydration with the addition of anhydrous magnesium sulfate, and then, distilled under a reduced pressure to remove therefrom isopropyl ether. With the addition of hexane as a poor solvent to the distillation residue, the fluorine-containing polymerizable monomer was precipitated. It was confirmed by DI-MS analysis that the solid precipitate was a mixture of the fluorine-containing polymerizable monomer of the formula (G) (HFIP-monosubstituted product) and the fluorine-containing polymerizable monomer of the formula (F) (HFIP-disubstituted product) at a ratio of F:G=2:3.

The analysis results of the fluorine-containing polymerizable monomer of the formula (F) are indicated below.

DI-MS (FD+): m/z 550.35 (M+), 384.45 (M+)

[Synthesis of Polymer Compounds]

Example 4

In a stirrer-equipped reaction vessel, 25.91 g (0.0500 mol) of the fluorine-containing polymerizable monomer of the formula (3) synthesized in Example 1, i.e., 3,3-bis(1,1,1,3,3,3-hexafluoro-2-hydroxypropane-2-yl)-4,4'-biphenol was prepared and dissolved in a dehydrated mixed solvent of 167 g of N-methylpyrrolidone and 8.7 g of pyridine. To this solution, 10.15 g (0.0500 mol) of isophthalic acid chloride was added. The resulting solution was subjected to condensation polymerization, as indicated in the following reaction scheme, by stirring for 5 hours at room temperature.

After the completion of the reaction, the reaction solution was gradually dropped into 1.5 kg of 50 mass % aqueous methanol solution as a poor solvent within a large-sized beaker to thereby form a polymer precipitate. The polymer precipitate was filtered out and dried under a reduced pressure at 100° C. for 8 hours in a vacuum drying oven. There was thus obtained 27.5 g of polyarylate resin having a repeating unit of the formula (H) as a product of the condensation product. The yield of the polyarylate resin was 85%.

Example 5

In a stirrer-equipped reaction vessel, 3.00 g (0.0052 mol) of the fluorine-containing polymerizable monomer of the formula (3) synthesized in Example 1, i.e., 3,3-bis(1,1,1,3,3,3-hexafluoro-2-hydroxypropane-2-yl)-4,4'-biphenol was prepared and dissolved in a dehydrated mixed solvent of 16 g of N-methylpyrrolidone and 1.01 g of pyridine. To this solution, 0.527 g (0.0026 mol) of isophthalic acid chloride and 0.527 g (0.0026 mol) of terephthalic acid chloride were added. The resulting solution was subjected to condensation polymerization, as indicated in the following reaction scheme, by stirring for 5 hours at room temperature.

After the completion of the reaction, the same operation as in Example 4 was carried out. There was thus obtained 3.28 g of polyarylate resin having a repeating unit of the formula (H) or (I) as a product of the condensation polymerization. The yield of the polyarylate resin was 90%.

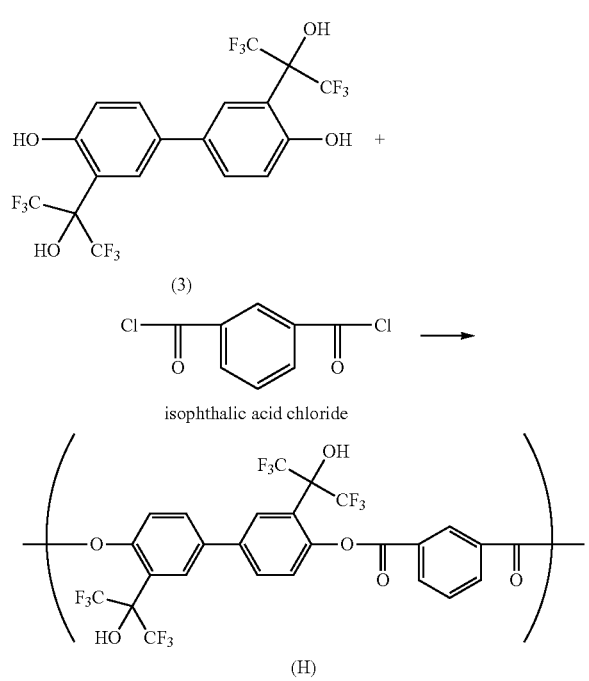

(3)

isophthalic acid chloride (H)

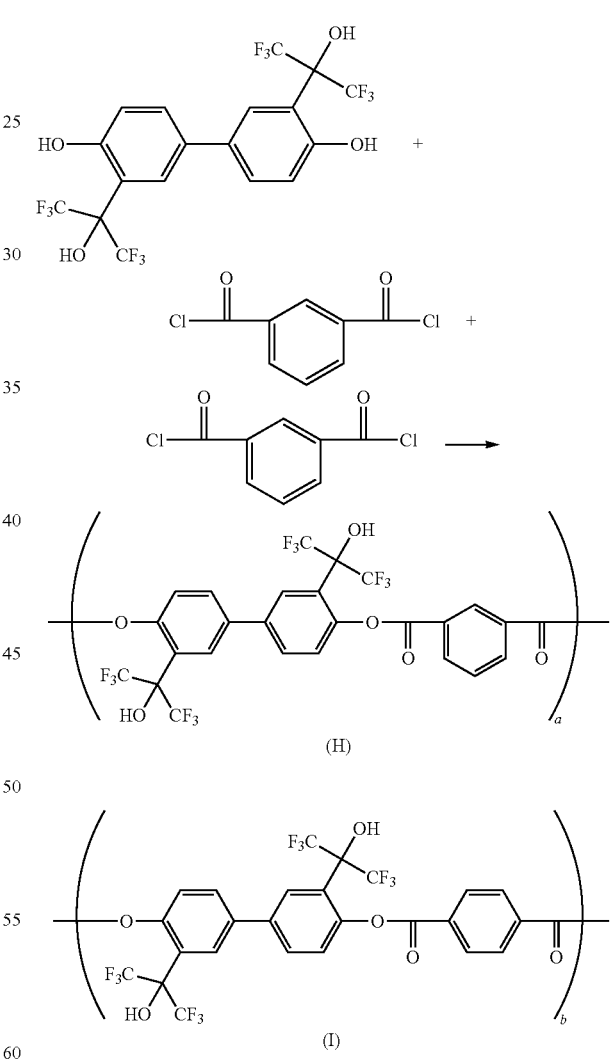

(H)

(I)

Example 6

In a stirrer-equipped reaction vessel, 3.00 g (0.0052 mol) of the fluorine-containing polymerizable monomer of the formula (3) synthesized in Example 1, i.e., 3,3-bis(1,1,1,3, 3,3-hexafluoro-2-hydroxypropane-2-yl)-4,4'-biphenol was prepared and dissolved in a dehydrated mixed solvent of 16 g of N-methylpyrrolidone and 1.01 g of pyridine. To this solution, 2.23 g (0.0052 mol) of 2,2-bis(4-carbonylchloride phenyl)hexafluoropropane was added. The resulting solution was subjected to condensation polymerization, as indicated in the following reaction scheme, by stirring for 5 hours at room temperature.

After the completion of the reaction, the same operation as in Example 4 was carried out. There was thus obtained 3.86 g of polyarylate resin having a repeating unit of the formula (P) as a product of the condensation polymerization. The yield of the polyarylate resin was 85%.

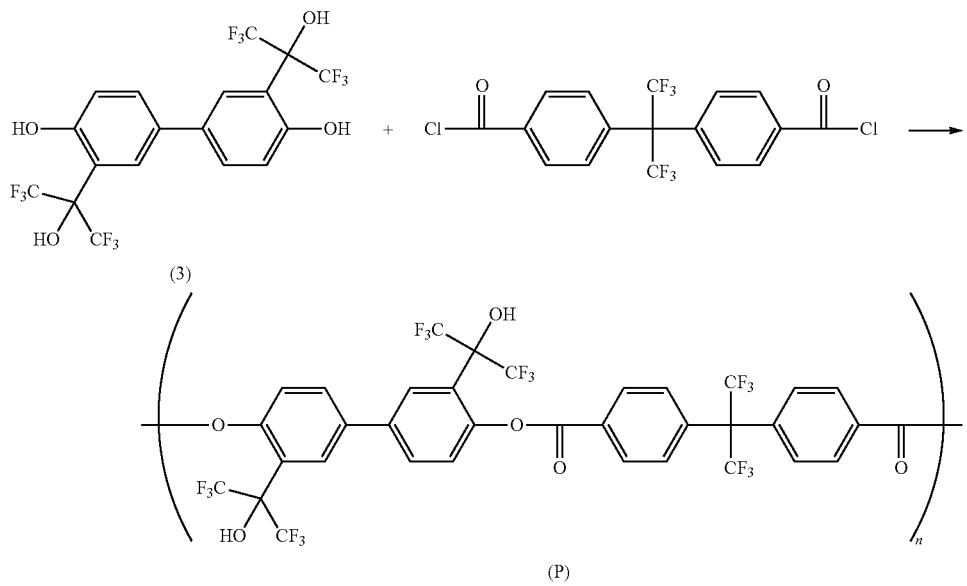

Example 7

In a stirrer-equipped reaction vessel, 2.26 g (0.0052 mol) of the mixture of the fluorine-containing polymerizable monomers (C) and (D) synthesized in Example 2 (C:D=2:3 in units of mol ratio) was prepared and dissolved in a dehydrated mixed solvent of 16 g of N-methylpyrrolidone and 1.01 g of pyridine. To this solution, 1.45 g (0.0052 mol) of 4,4'-biphenyl dicarbonyl dichloride was added. The resulting solution was subjected to condensation polymerization, as indicated in the following reaction scheme, by stirring for 5 hours at room temperature.

After the completion of the reaction, the same operation as in Example 4 was carried out. There was thus obtained 2.89 g of polyarylate resin having a repeating unit of the formula (R) as a product of the condensation polymerization. The yield of the polyarylate resin was 87%.

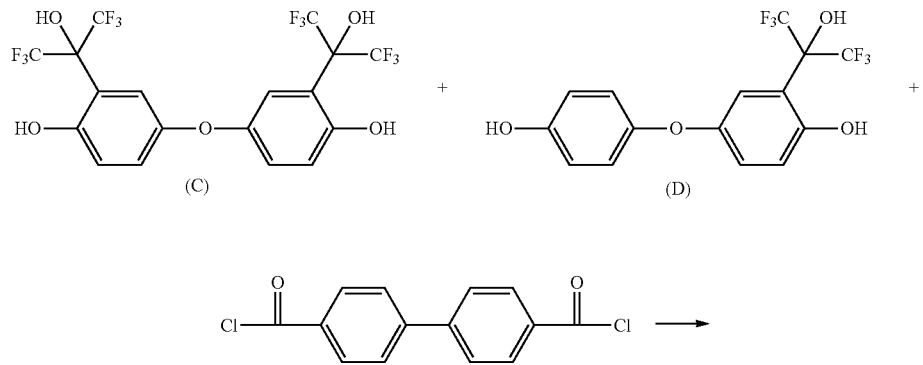

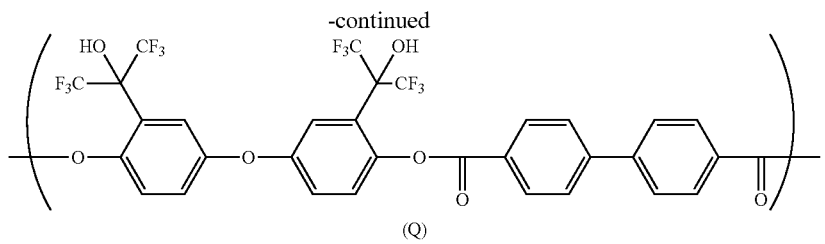

(Q)

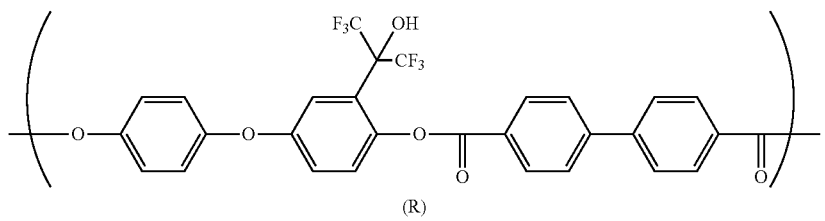

(R)

Example 8

In a stirrer-equipped reaction vessel, 1.036 g (0.00200 mol) of the fluorine-containing polymerizable monomer of the formula (3) synthesized in Example 1, i.e., 3,3-bis(1,1,1,3,3,3-hexafluoro-2-hydroxypropane-2-yl)-4,4'-biphenol was prepared and dissolved in a dehydrated mixed solvent of 7.0 g of N-methylpyrrolidone and 0.35 g of pyridine. To this solution, 0.436 g (0.00200 mol) of pyromellitic anhydride was added. The resulting solution was subjected to condensation polymerization, as indicated in the following reaction scheme, by stirring for 24 hours at room temperature.

After the completion of the reaction, the same operation as in Example 4 was carried out. There was thus obtained 1.22 g of polyarylate resin having a repeating unit of the formula (J) as a product of the condensation polymerization. The yield of the polyarylate resin was 83%. The molecular weight and solubility evaluation result of the polyarylate resin are indicated in TABLE 1.

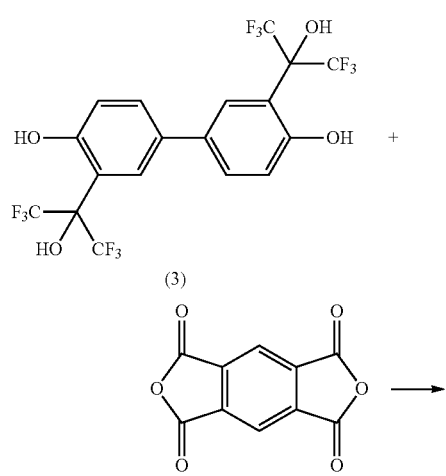

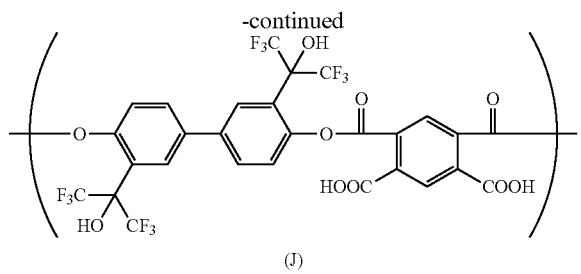

(J)

Example 9

In a stirrer-equipped reaction vessel, 1.036 g (0.002 mol) of the fluorine-containing polymerizable monomer of the formula (3) synthesized in Example 1, i.e., 3,3-bis(1,1,1,3,3,3-hexafluoro-2-hydroxypropane-2-yl)-4,4'-biphenol was prepared and dissolved in a dehydrated mixed solvent of 7.0 g of N-methylpyrrolidone and 0.35 g of pyridine. To this solution, 0.888 g (0.002 mol) of 2,2-bis(3,4-dicarboxyphenyl)hexafluoropropane dianhydride was added. The resulting solution was subjected to condensation polymerization, as indicated in the following reaction scheme, by stirring for 24 hours at room temperature.

After the completion of the reaction, the same operation as in Example 4 was carried out. There was thus obtained 1.73 g of polyarylate resin having a repeating unit of the formula (S) as a product of the condensation polymerization. The yield of the polyarylate resin was 90%. The molecular weight and solubility evaluation result of the polyarylate resin are indicated in TABLE 1.

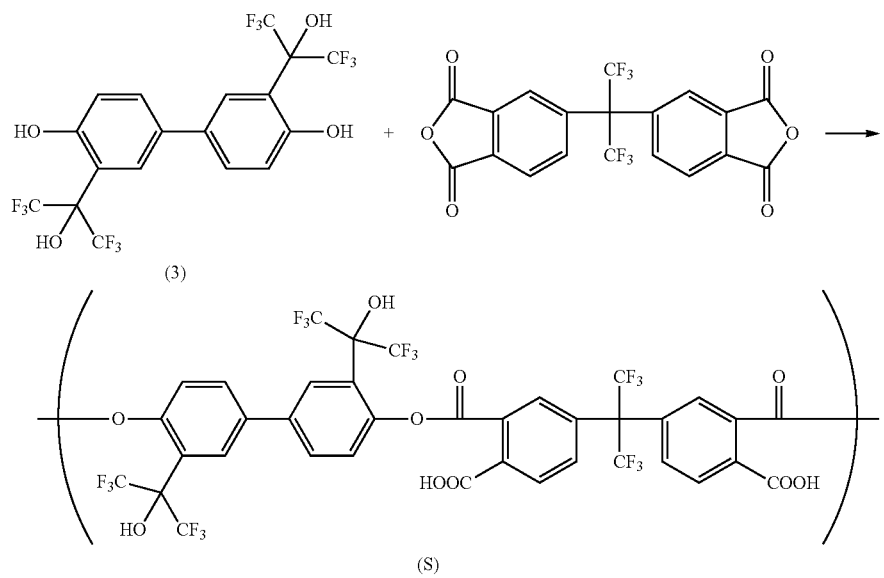

(3)

(S)

Comparative Example 1

In a stirrer-equipped reaction vessel, 0.931 g (0.00500 mol) of 4,4-biphenol was dissolved in a dehydrated mixed solvent of 8.6 g of N-methylpyrrolidone and 0.87 g of pyridine. To this solution, 1.015 g (0.00500 mol) of isophthalic acid chloride was added. The resulting solution was subjected to condensation polymerization, as indicated in the following reaction scheme, by stirring at room temperature (20° C.). Then, a precipitate occurred at 1 hour after the initiation of the stirring.

After the subsequent 3 hours of stirring, the reaction solution with the precipitate was gradually dropped into 100 g of methanol as a poor solvent within a beaker to further precipitate a polymer. The polymer precipitate was dried under a reduced pressure at 100° C. for 8 hours in a vacuum drying oven. There was thus obtained a polyarylate resin having a repeating unit of the formula (K). The obtained polyarylate resin was insoluble in organic solvents so that it was impossible to perform molecular weight determination and transparency evaluation of the polyarylate resin.

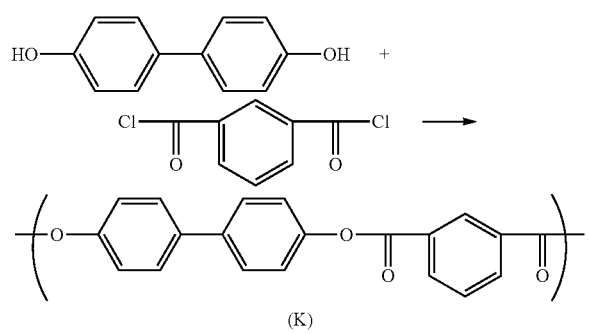

(K)

The polymer compounds of Examples 4 to 9 and Comparative Example 1 were evaluated for the solubility in NMP, cyclohexanone and TMAH by the above-indicated method. The weight-average molecular weight (Mw), molecular-weight distribution (Mw/Mn) and solubility evaluation results of the respective polymer compounds are indicated in TABLE 1.

TABLE 1

| | | Solubility | | |
|---|---|---|---|---|
| | Mw (Mw/Mn) | NMP | cyclohexanone | TMAH |
| Example 4 | 29000 (2.5) | ○ | ○ | ○ |
| Example 5 | 47000 (2.8) | ○ | ○ | ○ |
| Example 6 | 32000 (2.7) | ○ | ○ | ○ |
| Example 7 | 25000 (2.4) | ○ | ○ | ○ |
| Example 8 | 9000 (2.7) | ○ | ○ | ○ |
| Example 9 | 15000 (3.0) | ○ | ○ | ○ |
| Comparative Example 1 | unmeasureable | x | x | x |

NMP: n-methylpyrrolidone
TMAH: tetramethylammonium hydroxide
○: soluble
x: insoluble As shown in TABLE 1, each of the polyarylate resins of Examples 4 to 8 obtained as the HFIP-containing polymer compound according to the present invention was different from the polyarylate resin of Comparative Example 1 obtained as the polymer compound with no HFIP group, in that the polyarylate resins of Examples 4 to 8 were soluble in n-methylpyrrolidone, cyclohexanone and tetramethylammonium hydroxide and thus were easier to handle as functional resins or raw materials in the field of semiconductors etc. because of their organic solvent solubility.

Example 10

To 1.62 g of the polyarylate resin synthesized in Example 4, 1.28 g of bisphenol A type epoxy resin ("JER828" available from Mitsubishi Chemical Corporation) as an epoxy compound, 0.05 g of triphenylphosphine as a curing acceleration agent and 11.3 g of cyclohexanone were added. The solutes were dissolved in the solvent by stirring, thereby yielding a solution with a solid content of 20 mass %. The solution was dropped and spin-coated by a spin coater onto glass substrates at 1000 rpm for 40 seconds. The resulting coating films were dried at 80° C. for 5 minutes and cured by heating at 180° C. for 1 hour. By this, the cured films were formed on the respective glass substrates.

The glass substrate coated with the cured film was then tested for the light transmittance at 400 nm wavelength by means of the spectrophotometer using the glass substrate as a reference.

The two glass substrates with the cured films were additionally respectively heated for 30 minutes at 250° C. and 300° C. and tested for the light transmittance at 400 nm wavelength.

The thickness of the film after the heating at 180° C. and the thickness of the film after the additional heating were also measured. The residual film ratio was determined as the ratio of the thickness of the film after the additional heating assuming the thickness of the film after the heating at 180° C. as 100%. The higher the residual film ratio, the less the volatile content for higher film performance.

Then, 1.65 g of the above-obtained polyamide resin was mixed with 1.70 g of bisphenol A type epoxy resin ("JER828" available from Mitsubishi Chemical Corporation), 0.05 g of triphenylphosphine. To the resulting mixture, 13.6 g of NMP was added. The solute mixture was dissolved in the NMP solvent by stirring, thereby yielding a solution with a solid content of 20 mass %.

Using the obtained solution, cured films were formed and tested for the light transmittance and residual film ratio in the same manner as in Example 10.

The test results of Example 10 and Comparative Example 2 are indicated in TABLE 2.

TABLE 2

|  | After heating at 180° C. | | After heating at 250° C. | | After heating at 300° C. | |
| --- | --- | --- | --- | --- | --- | --- |
|  | Residual film ratio | T %@400 nm | Residual film ratio | T %@400 nm | Residual film ratio | T %@400 nm |
| Example 10 | — | 99% | 96% | 97% | 81% | 80% |
| Comparative Example 2 | — | >99% | 92% | 98% | 80% | 54% |

T %@400 nm: light transmittance at 400 nm wavelength

Comparative Example 2

In a stirrer-equipped reaction vessel, 21.212 g (0.0400 mol) of 3,3-bis(1,1,1,3,3,3-hexafluoro-2-hydroxypropane-2-yl)-4,4-methylene dianiline was dissolved in 150 g of dehydrated NMP. To this solution, 9.745 g (0.0480 mol) of isophthalic acid chloride was added. The resulting solution was subjected to condensation polymerization, as indicated in the following reaction scheme, by stirring at room temperature.

After the completion of the reaction, the same operation as in Example 4 was carried out. There was thus obtained 23.0 g of polyamide resin having a repeating unit of the formula (L). The yield of the polyamide resin was 87%. The molecular weight of the polyamide resin was Mw (Mw/Mn)=18000 (2.6).

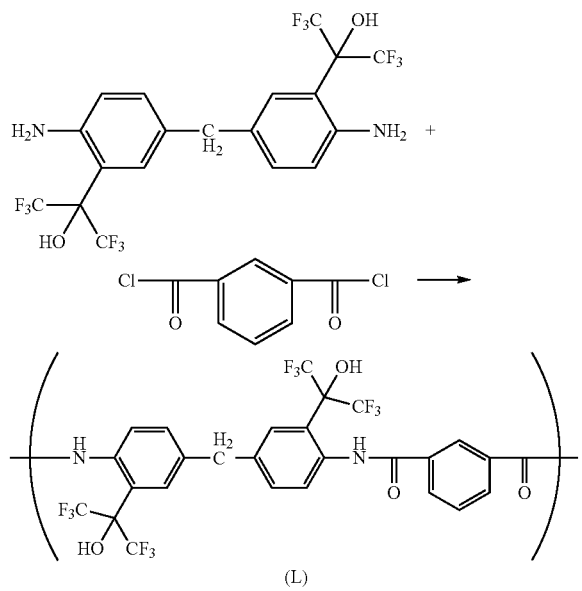

As shown in TABLE 2, the HFIP-containing polyarylate resin of Example 10 and the HFIP-containing polyamide resin of Comparative Example 2 had the same level of light transparency and residual film ratio after the heating at 250° C. However, the polyarylate resin of Example 10 was higher in transparency than the polyamide resin of Comparative Example 2 after the heating at 300 C. The reason for such difference in transparency is assumed that the polyamide resin was converted to have a structure of heterocyclic ring-containing repeating unit (M), as indicated in the following reaction scheme, so that the transparency of the polyamide resin was lowered with increase in the length of the π conjugated system.

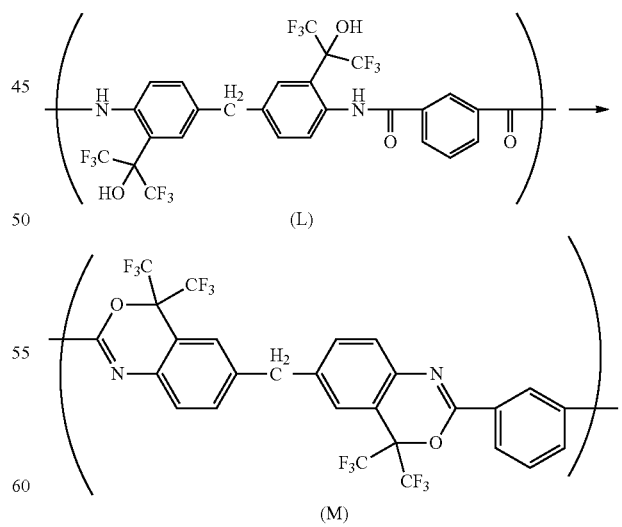

INDUSTRIAL APPLICABILITY

The fluorine-containing polymerizable monomer according to the present invention, which is characterized by having the HFIP group(s), is capable of condensation polymerization due to the presence of a plurality of hydroxy groups. The use of such a fluorine-containing polymerizable monomer makes it possible to introduce the HFIP group(s) into the chemical structure of the polyester resin and impart high transparency, low water absorption, low dielectric constant, low refractive index, good solvent solubility, good substrate adhesion etc. to the polyester resin. The polyester resin using the fluorine-containing polymerizable monomer according to the present invention is thus suitable for use in the field of polymer materials such as coatings for high-technology flat panel displays, protection films for substrates in electronic circuit boards, protection films for semiconductors and the like.

Although the present invention has been described above with reference to the specific exemplary embodiment, the present invention is not limited to the above-described exemplary embodiment. Various modifications and variations of the embodiment described above will occur within the scope of the present invention based on the common knowledge of those skilled in the art.

The invention claimed is:

1. A polymer compound having a repeating unit of the general formula (8):

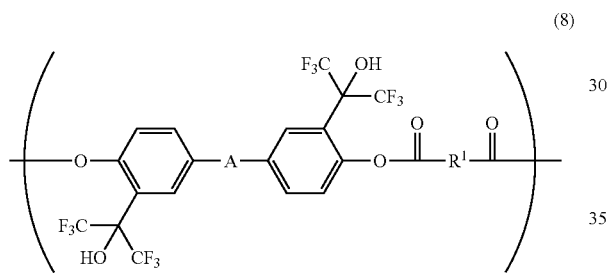

(8)

where A represents a single bond; $R^1$ represents an alkylene group or a divalent organic group obtained by elimination of two hydrogen atoms from an aromatic ring or an alicyclic ring; and $R^1$ may contain an oxygen atom, a sulfur atom or a nitrogen atom in its structure, and may have a part of hydrogen atoms substituted with a fluorine atom, a chlorine atom, an alkyl group or a fluoroalkyl group.

2. The polymer compound according to claim 1, wherein the repeating unit of the general formula (8) is of the formula (9):

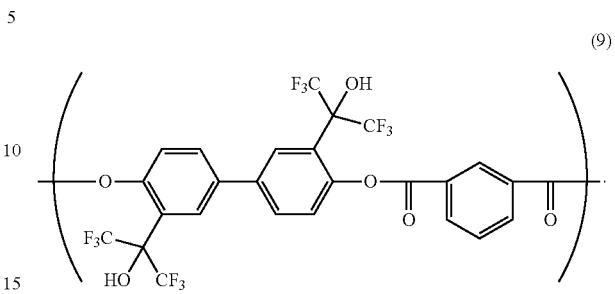

(9)

3. The polymer compound according to claim 1, wherein at least a part of hydrogen atoms of OH sites of 2-hydroxy-1,1,1,3,3,3-hexafluoroisopropyl groups is substituted with a glycidyl group.

4. A cured product obtained by cross-linking of the glycidyl group of the polymer compound according to claim 3.

5. The polymer compound according to claim 1, wherein $R^1$ is any one of the following structures:

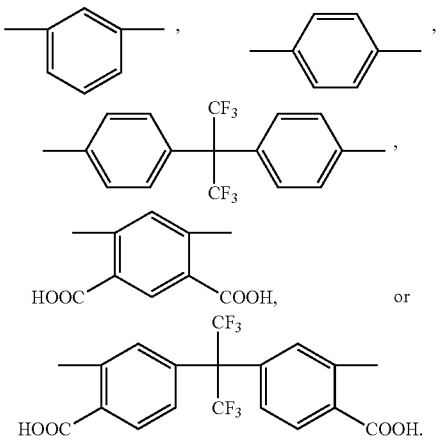

* * * * *